United States Patent [19]

Husemeyer et al.

[11] Patent Number: 4,840,639
[45] Date of Patent: Jun. 20, 1989

[54] AGENT FOR DYEING HAIR

[75] Inventors: Hans Husemeyer, Darmstadt, Fed. Rep. of Germany; Herbert Mager, Fribourg, Switzerland; Eugen Konrad, Darmstadt, Fed. Rep. of Germany

[73] Assignee: Wella Aktiengesellschaft, Darmstadt, Fed. Rep. of Germany

[21] Appl. No.: 204,993

[22] Filed: Jun. 7, 1988

Related U.S. Application Data

[63] Continuation of Ser. No. 901,994, Aug. 28, 1986, abandoned, which is a continuation of Ser. No. 669,634, Nov. 7, 1984, abandoned, which is a continuation of Ser. No. 433,728, Oct. 12, 1982, abandoned, which is a continuation of Ser. No. 253,636, Mar. 20, 1980, abandoned.

[30] Foreign Application Priority Data

Jul. 20, 1978 [DE] Fed. Rep. of Germany ....... 2831847

[51] Int. Cl.$^4$ ................................................. A61K 7/13
[52] U.S. Cl. ........................................... 8/410; 8/406; 8/407; 8/411; 8/412
[58] Field of Search ................... 8/406, 407, 410, 411, 8/412

[56] References Cited

U.S. PATENT DOCUMENTS

| | | | |
|---|---|---|---|
| 2,273,564 | 2/1942 | Dickey et al. | 560/251 |
| 3,820,948 | 6/1974 | Berth | 8/409 |
| 3,893,803 | 7/1975 | Kaiser | 8/410 |
| 4,425,132 | 1/1984 | Grollier et al. | 8/406 |
| 4,452,603 | 6/1984 | Konrad et al. | 8/406 |

FOREIGN PATENT DOCUMENTS

| | | | |
|---|---|---|---|
| 2155390 | 5/1972 | Fed. Rep. of Germany | 8/405 |
| 2215303 | 10/1972 | Fed. Rep. of Germany | 8/405 |

*Primary Examiner*—Dale R. Ore
*Attorney, Agent, or Firm*—Michael J. Striker

[57] ABSTRACT

Oxidative hair dyeing preparation having a content of a 1-hydroxyalkyl-2,5-diaminobenzene having the formula

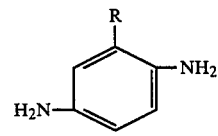

as developing substance, wherein R denotes hydroxyalkyl having 1 to 4 carbon atoms, or their salts with inorganic or organic acids. Preferably, these hair dyeing preparations will contain 1-hydroxymethyl-2,5-diaminobenzene in a concentration of approximately 0.1 to 3.0 percent by weight, this either alone as a developing substance, or in combination with the conventional coupling substances.

9 Claims, No Drawings

AGENT FOR DYEING HAIR

This application is a continuation, of application Ser. No. 901,994, filed Aug. 28, 1986 which is a continuation application of Ser. No. 669,634 filed Nov. 7, 1984, which is a continuation application of Ser. No. 433,728 filed Oct. 12, 1982 which is in turn a continuation application of Ser. No. 253,636 filed Mar. 20, 1980.

The object of the invention is preparations for the oxidative dyeing of hair on the basis of 1-hydroxyalkyl-2,5-diaminobenzenes as developing substances.

Oxidative colorants have obtained an essential importance in the field of hair dyeing. Dyeing results herein by the reaction of certain developing substances with certain coupling substances in the presence of a suitable oxidant.

2,5-diaminotoluene, p-aminophenol and 1,4-diaminobenzene are used in particular as developing substances. Resorcinol, chloro-resorcinol, α-naphthol, m-aminophenol and derivatives of m-phenylene diamine are examples of preferred coupling agents.

Numerous special demands are required to be met by oxidative colorants used in the dyeing of human hair. They must be unobjectionable as to toxicology and dermatology and enable dyeing to the desired intensity. It is furthermore required that a wide range of different tints be provided for by the combination of suitable developing and coupling constituents. The resultant hair colorings should, to a good degree, be fast to light and resistant to permanent-wave treatment, acids and rubbing. Such hair colorings must, at any rate, remain stable against the influence of light, rubbing and chemical agents, for a period of at least four weeks.

Developing substances as used at present in hair dyeing preparations, and the developing substances recently proposed for use, such as for instance pyrimidine derivatives, can not to date satisfactorily fulfill the aforenoted requirements.

The task existed therefore to locate suitable developing substances satisfying the aforenoted requirements to a high degree.

It was found in this context that preparations for the oxidative dyeing of human hair, will be of outstanding suitability, if they are characterized by having as developing substances at least one 1-hydroxyalkyl-2,5-diaminobenzene of the general formula

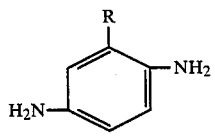

in which R denotes a hydroxyalkyl having 1 to 4 carbon atoms, or a salt thereof with an organic or inorganic acid, and which may be present in admixture with a conventional coupling agent.

As conventional coupling substances, α-naphthol, 3,4-diaminobenzoic acid, resorcinol, 4-chloro-resorcinol, m-aminophenol, m-phenylenediamine, m-toluylene diamine, 2,4-diamine anisol, 2,4-diaminobenzyl alcohol and 3-amino-6-methyl phenol or mixtures thereof may be taken into consideration as constituents of customary hair dyeing preparations.

The 1-hydroxy-alkyl-2,5-diaminobenzenes as above set out are excellently soluble in water and have a long shelf life, particularly as constituents of the hair dyeing preparations in accordance with invention.

These developing substances, of which the 1-hydroxymethyl-2,5-diaminobenzene is preferred, should be present in the hair dyeing preparations in a concentration of approximately 0.01 to 3.00 percent by weight, preferably 0.1 to 3.0 percent by weight. The total quantity of oxidative colorants, consisting of developing substances add the usual coupling substances will suitably amount to approximately 0.1 to 5.0 percent by weight, 0.5 to 3.0 percent by weight in particular.

The developing constituent is generally used in equimolar quantities relative to the coupling constituents. It will, however, not be of disadvantage if the developing constituent, in relation thereto, will be present either in a certain excess or with a certain deficiency.

Beyond this, the hair dyeing preparations noted in the present application, may also contain other known and usual developing substances and furthermore also conventional direct-acting colorants in their mixture, should this be required for the development of certain color tints.

The hair-dyeing preparation may furthermore also contain the usual cosmetic additives, for instance antioxidants such as ascorbic acid or sodium sulfite, perfume oils, complex-forming agents, emulsifiers, thickeners, hair-care substances and others.

The preparation may be made available as a solution, preferably in the form of a cream, a gel or an emulsion. Its composition represents a mixture of the colorant constituents with such constituents as are usual for such preparations. The usual constituents of creams, emulsions and gels which come into consideration herein will, for instance, be wetting agents or emulsifying agents from the categories of anionic or non-ionogenic surfactants such as sulfates of fatty alcohols, alkanolamides of fatty alcohols, alkyl sulfonates, alkylbenzene sulfonates, oxethylated fatty alcohols, oxethylated nonylphenols, furthermore thickeners such as higher fatty alcohols, starch, cellulose derivatives, paraffin oil and fatty acids, as well as hair-care substances such as lanolin derivatives, cholesterol and pantothenic acid.

The constituents as noted are used in the usual amounts for these purposes, i.e. emulsifying agents and wetting agents in concentrations of approximately 0.5 to 30 percent by weight, while thickeners may be present in the finished preparation in a quantity of approximately 0.1 to 25 percent by weight.

Depending on the formulated composition, the dyeing preparations in accordance with invention may react weakly acidic, neutral or alkaline. They have, in particular a pH value between 8.0 and 11.5 in the alkaline range, adjustment being preferably made with ammonia. Organic amines, such as, for instance, monoethanolamine or triethanolamine may also be used for this purpose.

The application of the dyeing agents is made in the known manner, by mixing the hair dyeing preparation with an oxidant shortly before use and applying the mixture onto the hair. In the main, it is hydrogen peroxide that is used as oxidant for the developing of the hair color, for instance as a 6% solution or as an additive compound with urea, melamine or sodium borate. The application temperatures are in the range of 15° to 50° C.

After an application period of approximately 10 to 45 minutes, preferably approximately 30 minutes, the hair is rinsed with water and dries. In given instances, washing with a shampoo may be performed subsequent to their rinse, and a final rinse made with a weak organic acid such as, for instance, tartaric acid or citric acid.

The preparation of the 1-hydroxyalkyl-2,5-diaminobenzene used as set out herein in accordance with the invention, is already known from literature and may be carried out in various ways. Thus, one may, for instance, proceed in the production of 1-hydroxymethyl-2,5-diaminobenzene from O-aminobenzyl alcohol. This is first acetylated and subsequently nitrated. By catalytic hydration of the resultant nitro compound and subsequent deacetylation, the 1-hydroxymethyl-2,5-diaminobenzene becomes available.

The hair dyeing preparations, in accordance with invention on the basis of 1-hydroxyalkyl-2,5-diaminobenzene as developing substance will bring about hair coloring with excellent properties as to fastness, especially fastness to light and resistance to washing and rubbing, and they may be removed again with reducing agents.

Of particular importance herein is the progress, attained in toxicologic and dermatologic aspects by using in the hair dyeing agents in accordance with the present application 1-hydroxyalkyl-2,5-diaminobenzenes; it is based upon the hydroxyalkyl group bonded to the substituted benzene nucleus and the reduced solubility of lipoids as a result thereof.

Regarding the coloring possibilities, the hair dyeing agents as per invention will offer a wide range of varying color tints depending upon the type and composition of the colorant constituents and extending from blond to blue and black color tints with brown, purple, violet shades in between. The color tints are distinguished herein by their particular intensive color.

This will become readily evident in a comparison with hair dyeing agents containing as developing substance on the one hand the known 2,5-diaminotoluene, and on the other the 1-hydroxymethyl-2,5-diaminobenzene as disclosed in the application. While a purple shade will be obtained on oxidative dyeing of hair with a developer/coupler combination of 2,5-diaminotoluene/3-amino-6-methylphenol, the combination of 1-hydroxymethyl-2,5-diaminobenzene/3-amino-6-methylphenol will result in a purple-violet tint of a considerably fuller color. A deepening of color may be observed in an analogous manner when using the combination 1-hydroxymethyl-2,5-diaminobenzene/m-aminophenol instead of the combination 2,5-diaminotoluene/m-aminophenol.

The superior coloring properties of the hair dyeing preparations in accordance with the present application, are further evidenced by allowing the tinting of grayed hair that has not been subjected to prior chemical damage, without problems and with a covering strength that had been unattainable heretofore.

The object of the invention is to be explained more closely in the following embodiments:

| Embodiment 1 | Embodiments Hair dyeing preparation in gel form |
|---|---|
| 0.25 g | 1-hydroxymethyl-2,5-diaminebenzene |
| 0.15 g | sodium sulfite, anhydrous |
| 2.50 g | lauryl alcohol-diglycolethersulfate 28% aqueous solution |
| 0.50 g | hydroxyethyl cellulose, high-viscosity |
| 5.00 g | ammonia, 22% |
| 41.60 g | water |
| 50.00 g | |

10 g of the above hair dyeing preparation is mixed with 10 mL of a solution (6%) of hydrogen peroxide shortly before use and the mixture subsequently applied to natural-blond hair. After a treatment period of 30 minutes at 40° C., rinsing is carried out with water and the hair is then dried. The hair will be of a beige-blond coloring with a violet hue, conforming to fashion.

| Embodiment 2 | Hair dyeing preparation in gel form |
|---|---|
| 0.35 g | 1 hydroxymethyl-2,5-diaminobenzene |
| 0.27 g | resorcinol |
| 0.30 g | ascorbic acid |
| 15.00 g | oleic acid |
| 7.00 g | isopropanol |
| 10.00 g | ammonia, 22% |
| 67.08 g | water |
| 100.00 g | |

10 g of the above hair dyeing preparation are mixed with 10 mL of a solution (6%) of hydrogen peroxide shortly before use, and the mixture is allowed to act upon the natural-blond hair for 30 minutes at 40° C. Rinsing is then carried out with water and the hair is then dried. The hair is dyed in a very natural dark-blond color tint.

| Embodiment 3 | Hair dyeing preparation as cream |
|---|---|
| 0.35 g | 1-hydroxymethyl-2,5-diaminobenzene |
| 0.27 g | m-phenylene diamine |
| 15.00 g | cetyl alcohol |
| 0.30 g | sodium sulfite, anhydrous |
| 3.50 g | lauryl alcohol-diglycol ether sulfate 28% aqueous solution |
| 3.00 g | ammonia, 22% |
| 77.58 g | water |
| 100.00 g | |

10 g of this hair dyeing agent are mixed with 10 mL of a solution (6%) of hydrogen peroxide shortly before application. The mixture is subsequently applied to natural blond hair and allowed to act for 30 minutes at 40° C. Rinsing is then carried out with water and the hair dried thereafter. The hair has imparted thereof an intense blue coloring.

| Embodiment 4 | Hair dyeing solution |
|---|---|
| 1.00 g | 1-hydroxymethyl-2,5-diaminobenzene |
| 0.60 g | resorcinol |
| 0.30 g | m-aminophenol |
| 0.10 g | m-phenylene diamine |
| 10.00 g | lauryl alcohol-diglycol ether sulfate 28% aqueous solution |
| 10.00 g | ammonia, 22% |
| 78.00 g | water |
| 100.0 g | |

10 g of the aforenamed hair dyeing agent is mixed with 10 mL of a solution (6%) of hydrogen peroxide shortly before using, and the mixture is allowed to act on natural blond hair for 30 minutes at 40° C. Rinsing is then carried out with water and the hair dried thereafter. The hair is dyed to an intense blackish-brown tint.

| Embodiment 5 | Hair dyeing preparation in gel form |
|---|---|
| 0.25 g | 1-hydroxypropyl-2,5-diaminobenzene |
| 0.15 g | sodium sulfite, anhydrous |
| 2.50 g | lauryl alcohol-diglycol ether sulfate, 28% aqueous solution |
| 0.50 g | hydroxyethyl cellulose, high-viscosity |
| 5.00 g | ammonia, 22% |
| 91.60 g | water |
| 100.00 g | |

10 g of the above hair dyeing preparation are mixed with 10 mL hydrogen-peroxide (6% solution) shortly before use and the mixture subsequently applied to natural blond hair. After a treatment time of 30 minutes at 40° C., rinsing is carried out with water, and drying thereafter. The hair has imparted thereto a beige-blond coloring.

All quantities given in percent in the present application denote percentages by weight.

We claim:

1. A composition for use in the oxidative dyeing of human hair comprising 0.1 to 5.0 weight percent of a combination of
   (A) at least one coupler conventionally used in hair coloring selected from the group consisting of 2-napthol, 3,4-diamino-benzoic acid, resorcinol, 4-chlororesorcinol, m-aminophenol, m-phenylene diamine, n-toluylene diamine, 2,4-diamino anisol, 2,4-diamino benzyl alcohol and 3-amino-6-methyl-phenol; and
   (B) 0.01 to 3.0 weight percent of an 1-hydroxy-alkyl-2,5-diamino-benzene of the formula

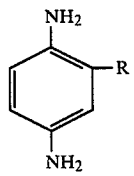

where R is a hydroxyalkyl having 1 to 2 carbon atoms as developer.

2. A composition as defined in claim 1, wherein said developer is 1-hydroxy-methyl-2,5-diamino benzene.

3. A composition as defined in claim 1, wherein said developer is 1-hydroxyethyl-2,5-diamino benzene.

4. A composition as defined in claim 1, wherein said developer is 1-hydroxymethyl-2,5-diamino benzene and said coupler is m-phenylene diamine.

5. A composition as defined in claim 1, wherein said developer is 1-hydroxymethyl-2,5-diamino benzene and said coupler is resorcinol.

6. A composition according to claim 1 in gel form having the following composition:

| 0.35 g | 1-hydroxymethyl-2,5-diaminobenzene |
|---|---|
| 0.27 g | resorcinol |
| 0.30 g | ascorbic acid |
| 15.00 g | oleic acid |
| 7.00 g | isopropanol |
| 10.00 g | ammonia (22%) |
| 67.08 g | water |
| 100.00 g. | |

7. A composition according to claim 1 in cream form having the following composition:

| 0.35 g | 1-hydroxymethyl-2,5-diaminobenzene |
|---|---|
| 0.27 g | m-phenylene diamine |
| 15.00 g | cetyl alcohol |
| 0.30 g | sodium sulfite, anhydrous |
| 3.50 g | lauryl alcohol - diglycol ether sulfate 28% aqueous solution |
| 3.00 g | ammonia, 22% |
| 77.58 g | water |
| 100.00 g. | |

8. A composition according to claim 1 in solution form having the following composition:

| 1.00 g | 1-hydroxymethyl-2,5-diaminobenzene |
|---|---|
| 0.60 g | resorcinol |
| 0.30 g | m-aminophenol |
| 0.10 g | m-phenylene diamine |
| 10.00 g | lauryl alcohol-diglycol ether sulfate 28% aqueous solution |
| 10.00 g | ammonia, 22% |
| 78.00 g | water |
| 100.00 g. | |

9. A process for the oxidative dyeing of human hair which comprises, shortly before use admixing about 10 g of a composition according to claim 1 with about 10 ml of a 6% solution of hydrogen peroxide or an addition compound thereof with one of urea, melamine or sodium borate, applying an effective amount of the resultant mixture for coloring the hair onto the hair, allowing it to remain on and in contact with the hair for from 10 to 45 minutes at a temperature of from 15° to 50° C., rinsing the hair with water and allowing the hair to dry.

* * * * *